(12) United States Patent
Jeong et al.

(10) Patent No.: US 9,658,145 B2
(45) Date of Patent: May 23, 2017

(54) DISPLAY DEVICE AND A METHOD OF MEASURING A STRAIN OF THE DISPLAY DEVICE

(71) Applicant: Samsung Display Co., Ltd., Yongin, Gyeonggi-Do (KR)

(72) Inventors: Chul-Woo Jeong, Hwaseong-si (KR); Soon-Ryong Park, Cheonan-si (KR); Seok-Gi Baek, Yongin-si (KR); Jung-Ho So, Cheonan-si (KR); Tae-Eun Kim, Cheonan-si (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 114 days.

(21) Appl. No.: 14/302,009

(22) Filed: Jun. 11, 2014

(65) Prior Publication Data
US 2015/0007669 A1    Jan. 8, 2015

(30) Foreign Application Priority Data
Jul. 3, 2013    (KR) ........................ 10-2013-0077626

(51) Int. Cl.
*G01N 3/20*    (2006.01)
*G01N 19/08*    (2006.01)
*G01N 33/00*    (2006.01)

(52) U.S. Cl.
CPC ....... *G01N 3/20* (2013.01); *G01N 2033/0078* (2013.01); *G01N 2033/0095* (2013.01)

(58) Field of Classification Search
CPC ............. G01N 3/20; G01N 2033/0095; G01N 2033/0078; G01N 21/958; G01N 3/12; G02B 5/003; G02B 5/0268; G02B 5/0294; G02B 27/26; C03C 8/02; C03C 2218/365; C03C 8/14; C03C 2218/119; G01L 1/22; G09G 3/20; G09G 2380/02; G09G 2330/04; G09G 2300/043; G09G 3/006; G02F 1/135; G06F 3/0416; G01B 7/16
USPC ................ 73/849, 778; 65/60.1, 60.53, 348; 356/225; 445/63; 345/173
See application file for complete search history.

(56) References Cited

U.S. PATENT DOCUMENTS

2005/0066721 A1 * 3/2005 Swillo ................... H04L 9/0852
73/159
2011/0222053 A1 * 9/2011 Kamikawa ................ C03C 8/02
356/225

FOREIGN PATENT DOCUMENTS

| KR | 1020040105481 A | 12/2004 |
| KR | 100666776 B1 | 1/2007 |
| KR | 1020090054696 A | 6/2009 |
| KR | 1020100119370 A | 11/2010 |

* cited by examiner

*Primary Examiner* — Harshad R Patel
*Assistant Examiner* — Brandi Hopkins
(74) *Attorney, Agent, or Firm* — Robert E. Bushnell, Esq.

(57) ABSTRACT

A measurement pigment composition including pigment particles may be coated on a surrounding area of a display panel to form a strain measuring part. A strain of the display device may be measured by using 3D images of the strain measuring part.

19 Claims, 5 Drawing Sheets

DISPLAY DEVICE AND A METHOD OF MEASURING A STRAIN OF THE DISPLAY DEVICE

CLAIM OF PRIORITY

This application claims priority under 35 U.S.C. §119 to Korean Patent Application No. 10-2013-0077626, filed on Jul. 3, 2013 in the Korean Intellectual Property Office (KIPO), the contents of which are herein incorporated by reference in its entirety.

BACKGROUND OF THE INVENTION

Field of the Invention

Embodiments of the present invention generally relate to a display device and a method of measuring a strain of the display device, and more particularly, to a display device having a strain measuring part and a method of measuring a strain of the display device.

Description of the Related Art

Recently, a flexible display is being developed to be used for electronic devices such as a mobile phone, a smart phone or a tablet personal computer. For achieving the flexible display, a display part of a display device also needs to be flexible.

However, when a display panel is bent in a manufacturing process, a defect such as a delamination between the display panel and a film disposed thereon may be caused.

SUMMARY OF THE INVENTION

One or more exemplary embodiment of the invention provides a quantitative method of measuring a strain of a display device.

One or more exemplary embodiment of the invention provides a display device including a strain measuring part.

According to another exemplary embodiment of the present invention, a method of measuring a strain of a display device is provided. According to the method, a measurement pigment composition including pigment particles may be coated on a surrounding area of a display panel to form a strain measuring part. A strain of the display device may be measured by using 3D images of the strain measuring part.

In an exemplary embodiment, a polarization film may be combined with the display panel. A driving part may be combined with the display panel at a side of the polarization film.

In an exemplary embodiment, the surrounding area of the display panel may include a first coating area, a second coating area and a third coating area. The first coating area may surround the driving part, the second coating area may surround the polarization film and the third coating area may be on a lower area of the display panel, which is opposite to an upper surface of the display panel where the polarization film and the driving part are disposed.

In an exemplary embodiment, the measurement pigment composition may be coated by a dispensing, a screen printing, a spin coating, a slit coating, a bar coating or a nozzle spraying to form the strain measuring part.

In an exemplary embodiment, the strain measuring part may include ultraviolet curable resin, thermoplastic resin and thermosetting resin.

In an exemplary embodiment, the pigment particles may include a black pigment and a white pigment.

In an exemplary embodiment, a strain may be measured by the steps of taking a first 3D image before the display device is bent, bending the display device, taking a second 3D image, comparing the first 3D image with the second 3D image, and determining a strain of the display device based on the comparison between the first 3D image and the second 3D image.

In an exemplary embodiment, a distance between the pigment particles may be measured to compare the 3D images.

According to exemplary embodiments of the present invention, a display device may include a display panel, a strain measuring part including pigment particles and disposed on a surrounding area of the display panel.

In an exemplary embodiment, the strain measuring part may include an ultraviolet curable resin, a thermoplastic resin or a thermosetting resin.

In an exemplary embodiment, the pigment particles may include lithopone, white lead or carbon black.

In an exemplary embodiment, the pigment particles may include $K_2O$, $Fe_2O_3$, $Sb_2O_3$, $ZnO$, $P_2O_5$, $V_2O_5$, $TiO_2$, $Al_2O_3$, $WO_3$, $SnO$, $PbO$, $MgO$, $CaO$, $BaO$, $Li_2O$, $Na_2O$, $B_2O_3$, $TeO_2$, $SiO_2$, $Ru_2O$, $Rb_2O$, $Rh_2O$, $CuO$, $Cr_2O3$, $Na_2S$ or $Bi_2O_3$.

In an exemplary embodiment, a size of each pigment particles may be about 0.1 μm to about 0.5 μm.

In an exemplary embodiment, a thickness of the display panel may be about 100 μm to about 500 μm.

In an exemplary embodiment, the display device may further include a polarization film disposed on the display panel and a driving part connected to the display panel.

In an exemplary embodiment, the strain measuring part may be further disposed on an upper surface of the display panel and to have a shape surrounding the polarization film in a plan view.

In an exemplary embodiment, the strain measuring part may be further disposed on a lower surface of the display panel.

According to the exemplary embodiments of the present invention, the display device may include a strain measuring part. Thus, a strain of the display panel may be measured.

According to the exemplary embodiments of the present invention, a display panel having a desired strain ratio can be designed. Thus, a defect of the display panel, which is due to an external pressure, may be prevented.

According to the exemplary embodiments of the present invention, when a display panel is bent, a delamination between the display panel and a film disposed thereon may be prevented.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein.

DETAILED DESCRIPTION OF THE INVENTION

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms. These terms are used to distinguish one element from another. Thus, a first element discussed below could be termed a second element without departing from the teachings of the present inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be explained in detail with reference to the accompanying drawings.

Figure 1:
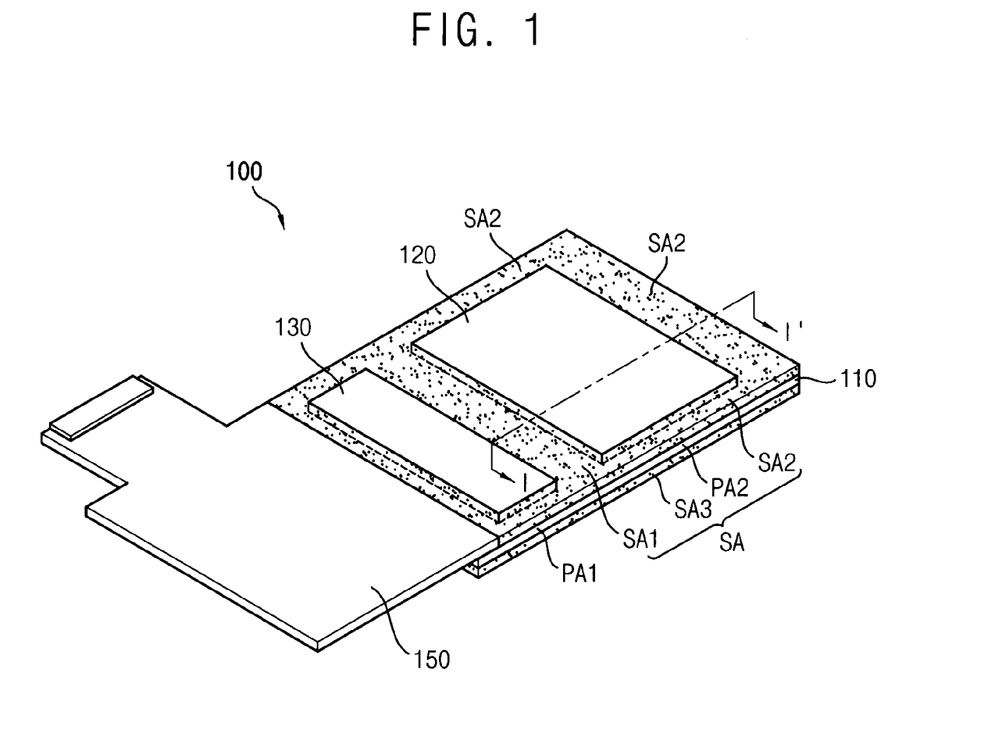
FIG. 1 is an oblique view illustrating a display device according to an exemplary embodiment of the present invention.
Figure 2:
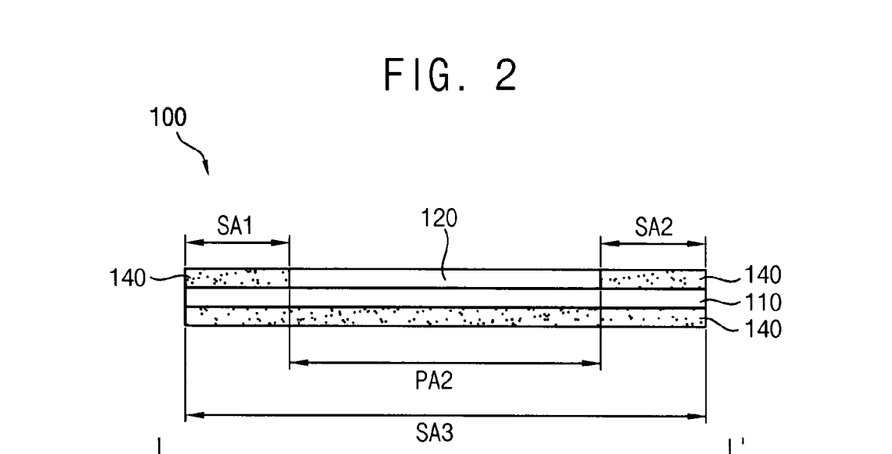
FIG. 2 is a cross-sectional view taken along a line I-I' of FIG. 1.

FIG. 1 is an oblique view illustrating a display device according to an exemplary embodiment of the present invention. FIG. 2 is a cross-sectional view taken along a line I-I' of FIG. 1.

Referring to FIGS. 1 and 2, a display device 100 includes a display panel 110, a polarization film 120, a driving part 130, a strain measuring part 140 disposed on a surrounding area SA and a flexible printed circuit board 150.

Examples of the display panel may include a liquid crystal display (LCD) panel, an organic light emitting display (OLED) panel, an electrophoresis display panel, a flexible display panel, and etc. A thickness of the display panel 110 may be about 100 μm to about 500 μm.

The polarization film 120 is disposed on a second panel area PA2 so that an image displayed in the second panel area PA2 may be viewed by a user.

The driving part 130 is disposed on a first panel area PA1 of the display panel 110. The driving part 130 is electrically connected to the display panel 110 and the flexible printed circuit board 150. An electric power source and signals transfer to the display panel 110 through the flexible printed circuit board 150 and the driving part 130.

The strain measuring part 140 is disposed on the surrounding area SA. The surrounding area may include a first coating area SA1, a second coating area SA2 and a third coating area SA3. The first coating area SA1 surrounds the driving part 130, the second coating area SA2 surrounds the polarization film 120 and the third coating area SA3 is on a lower surface of the display panel 110, which is opposite to an upper surface of the display panel where the polarization film 120 and the driving part 130 are disposed.

A thickness of the strain measuring part 140 may be about 5 μm to about 10 μm.

The strain measuring part 140 is formed from a measurement pigment composition. The measurement pigment composition may include an ultraviolet curable resin, a thermoplastic resin or a thermosetting resin. Preferably, the measurement pigment composition may include a urethaneacrylate resin or a polycarbonate resin. Thus, the strain measuring part 140 includes a pigment.

The measurement pigment composition may further include pigment particles. The pigment particles may include an organic pigment such as a lake pigment, color pigment. For example, the pigment particles may include lithopone, white lead or carbon black. These can be used alone or in a combination thereof.

The pigment particles may include an inorganic pigment such as a metal oxide or a sulfide. For example, the pigment particles may include $K_2O$, $Fe_2O_3$, $Sb_2O_3$, $ZnO$, $P_2O_5$, $V_2O_5$, $TiO_2$, $Al_2O_3$, $WO_3$, $SnO$, $PbO$, $MgO$, $CaO$, $BaO$, $Li_2O$, $Na_2O$, $B_2O_3$, $TeO_2$, $SiO_2$, $Ru_2O$, $Rb_2O$, $Rh_2O$, $CuO$, $Cr_2O3$, $Na_2S$ or $Bi_2O_3$.

In an exemplary embodiment of the present invention, the measurement pigment composition may include a mixture of a black color pigment particle and a white color pigment particle. A size of each pigment particle may be is about 0.1 μm to about 0.5 μm FIGS. 3 to 7 are cross-sectional views illustrating a method of measuring a strain of a display device illustrated in FIG. 1.

Figure 3:
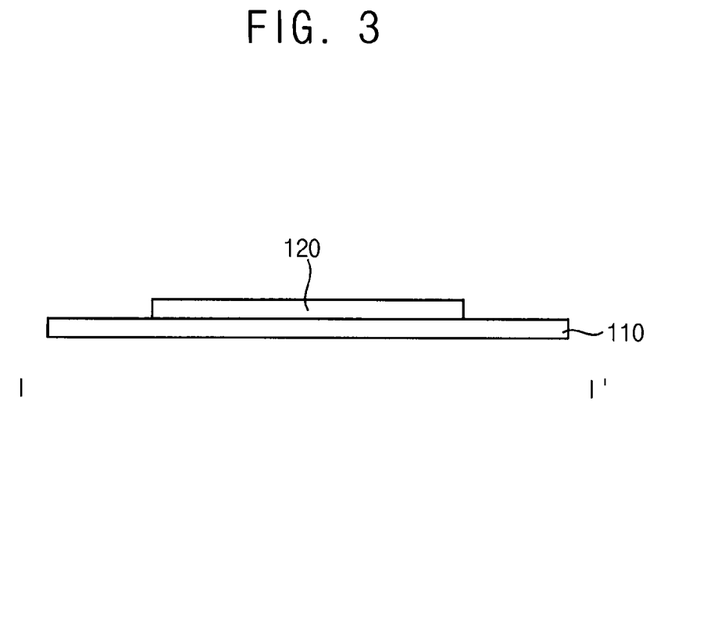
FIGS. 3 to 7 are cross-sectional views illustrating a method of measuring a strain of the display device illustrated in FIG. 1.

Referring to FIGS. 1 and 3, a polarization film 120 is combined with the display panel 110. A driving part 130 disposed at a side of the polarization film 120 and connected to the display panel 110 is combined with the display panel 110. The driving part 130 is connected to the display panel 110 or a flexible printed circuit board 150. An electric power source and signals transfer to the display panel 110 through the flexible printed circuit board 150 and the driving part 130.

Figure 4:
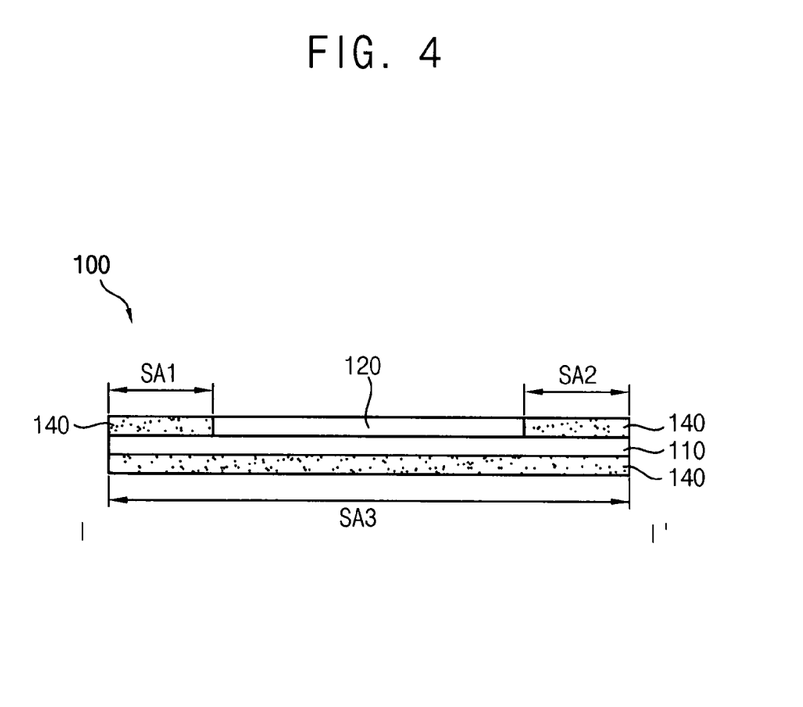

Referring to FIG. 4, a measurement pigment composition is coated on a surrounding area SA to form a strain measuring part 140. The surrounding area SA may include a first coating area SA1, a second coating area SA2 and a third coating area SA3. The first coating area SA1 surrounds the driving part 130, the second coating area SA2 surrounds the polarization film 120 and the third coating area SA3 is on a lower surface of the display panel 110, which is opposite to an upper surface of the display panel where the polarization film and the driving part are disposed. Thus, the measurement pigment composition is selectively coated on the first coating area SA1, the second coating area SA2 or the third coating area SA3.

The measurement pigment composition may include an ultraviolet curable resin, a thermoplastic resin and a thermosetting resin. Preferably, the measurement pigment composition may include a urethaneacrylate resin or a polycarbonate resin.

The measurement pigment composition is coated by a dispensing, a screen printing, a spin coating, a slit coating, a bar coating or a nozzle spraying to form the strain measuring part.

The measurement pigment composition may include pigment particles. The pigment particles may include an organic pigment such as a lake pigment, color pigment. For example, the pigment particles may include a lithopone, a white lead or a carbon black. These can be used alone or in a combination thereof.

The pigment particles may include an inorganic pigment such as a metal oxide or a sulfide. For example, the pigment particles may include $K_2O$, $Fe_2O_3$, $Sb_2O_3$, $ZnO$, $P_2O_5$, $V_2O_5$, $TiO_2$, $Al_2O_3$, $WO_3$, $SnO$, $PbO$, $MgO$, $CaO$, $BaO$, $Li_2O$, $Na_2O$, $B_2O_3$, $TeO_2$, $SiO_2$, $Ru_2O$, $Rb_2O$, $Rh_2O$, $CuO$, $Cr_2O3$, $Na_2S$ or $Bi_2O_3$.

In an exemplary embodiment of the present invention, the measurement pigment composition may include a mixture of a black color pigment particle and a white color pigment particle. A size of each pigment particle may be about 0.1 μm to about 0.5 μm.

A strain of the display device 100 may be measured by using of a sensor head, a monitor, a sensor controller, a processing computer or software.

Figure 5:
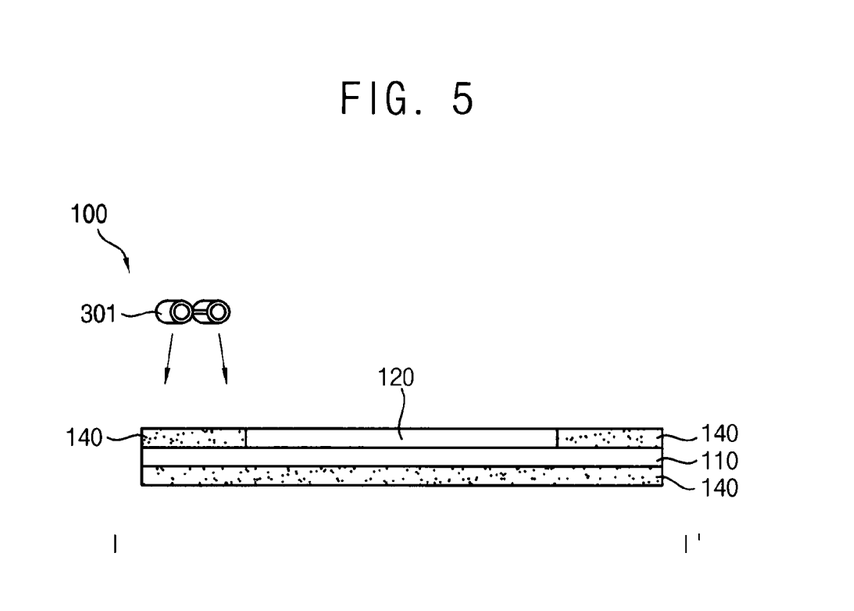

FIG. 5 represents photographing a display device 100, before the display device 100 is bent. Particularly, the display device 100 including a strain measuring part 140 is photographed by using a 3D image camera 301, before the display device 100 is bent.

Figure 6:
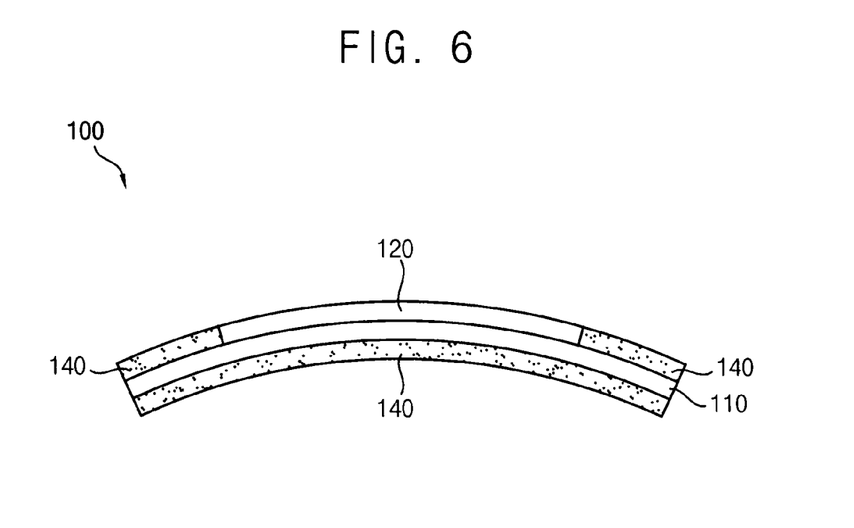

Referring to FIG. 6, the display device 100 is bent. A bending direction and a bending strength may be selectively changed by an operator measuring a strain of the display device 100.

Figure 7:
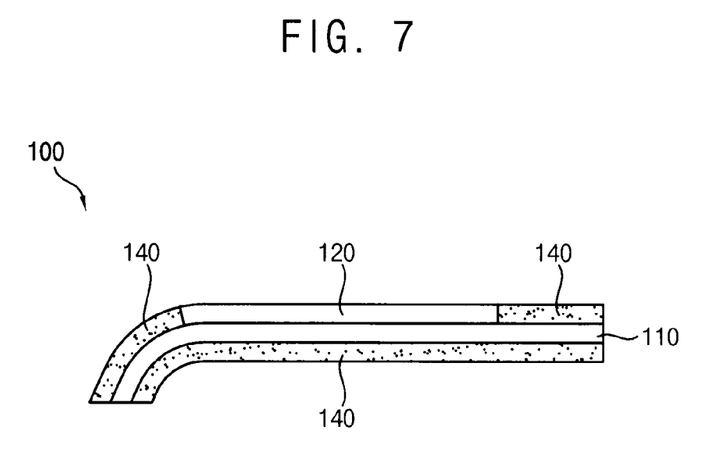

FIG. 7 represents photographing a display device 100 bent in a different direction by a different strength from the display device illustrated in FIG. 6. Particularly, a side portion of the display device 100 is bent in a direction. A bending direction and a bending strength may be selectively changed by an operator measuring a strain of the display device 100.

Figure 8:
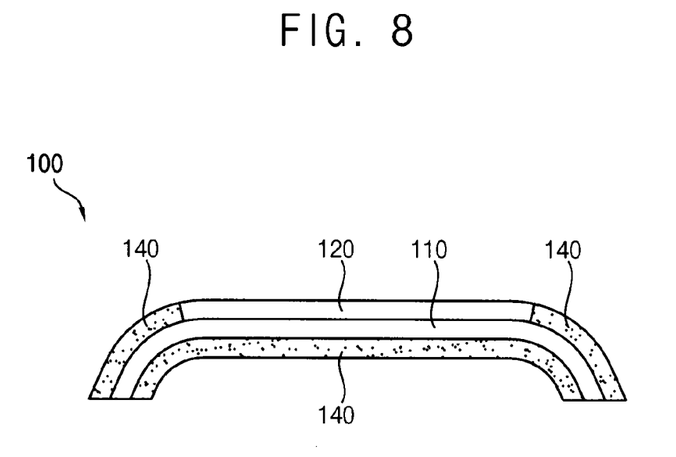
FIG. 8 is a cross-sectional view illustrating photographing a display device bent in a different direction by a different strength from the display device illustrated in FIG. 7.

FIG. 8 represents photographing a display device 100 bent in a different direction by a different strength from the display device illustrated in FIG. 7. Both side portions of the display device 100 are bent. A bending direction and a bending strength may be selectively changed by an operator measuring a strain of the display device 100.

Figure 9:
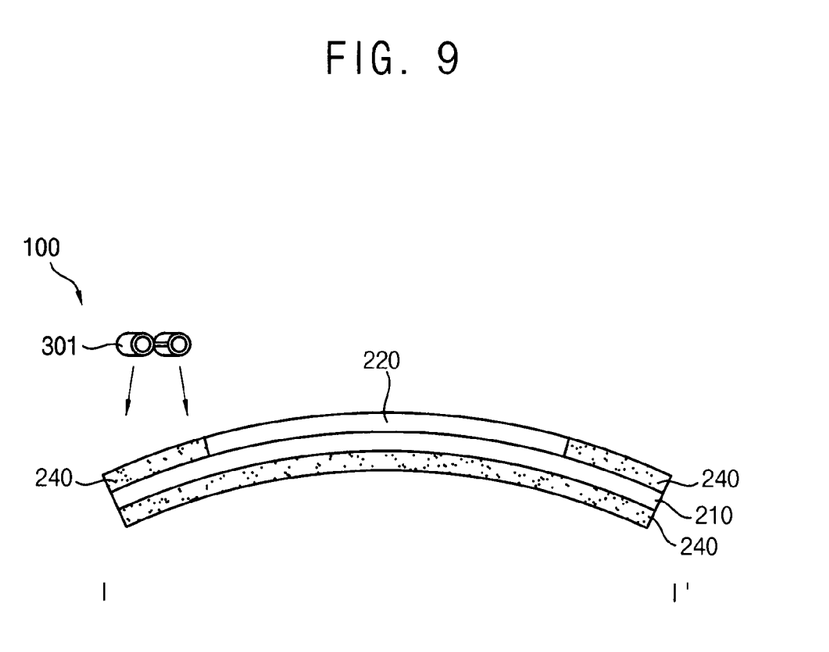
FIG. 9 a cross-sectional view illustrating photographing a display device after the display device is bent.

FIG. 9 represents photographing a display device 100, after the display device 100 is bent. The display device 100 including a strain measuring part 240 is photographed by using a 3D image camera 301, after the display device 100 is bent.

Images photographed by the 3D camera 301 are printed. The images, which are taken before the display device is bent and after the display device is bent, are compared by using a processing computer and software.

When the photographed images by the 3D camera 301 are compared, a stretched gap or a reduced gap between the pigment particles of the strain measuring part 140, 240 may be measured, so that a strain ratio of the display device 100 may be calculated therefrom. The measured strain of the display device may be represented a contour line shape or a quantified table. A size of the pigment particles is about under 1 μm. Preferably, a size of each pigment particles is about 0.1 μm to about 0.5 μm.

Table 1 represents a strain ratio of the display panel experimentally measured according to Example of the invention. Value 1 represents a strain ratio of a display panel having a thickness of 300 μm and including a polarization film, a protect film and a strain measuring part, before the display panel was bent. Value 2 represents a strain ratio of the display panel after the display panel was bent by a radius of curvature of 3 mm per 90 degrees. Value 3 represents a strain ratio of a display panel having a thickness of 600 μm and including an optically clear adhesive film having a thickness of 300 μm, a protect film and a strain measuring part, after the display panel was bent as a radius of curvature of 3 mm per 90 degrees.

A mixture of urethane acrylate and titanium oxide having a particle size of about 0.1 μm was used to form the strain measuring part. A 3D camera was used for photographing the display panel.

TABLE 1

| Category | A strain ratio (%) |
|---|---|
| Value 1 | 0% |
| Value 2 | 1.0% |
| Value 3 | 1.5% |

Referring to TABLE 1, Value 2 is increased by about 1.0% than Value 1. Value 3 is increased by about 1.5% than Value 1. Thus, it can be noted that a strain of a display device may be quantitatively measured by using the strain measuring part disposed on a peripheral area and formed from the measurement pigment composition. Therefore, a reliability of the display device may be improved.

According to the exemplary embodiments of the present invention, a display panel includes a strain measuring part. Thus, a strain of a display panel may be measured after the display panel is bent.

According to the exemplary embodiments of the present invention, a display panel having a desired strain ratio can be designed. Thus, a defect of the display panel, which is due to an external pressure, may be prevented.

According to the exemplary embodiments of the present invention, delamination films disposed on and under the display panel may be prevented when the display panel is bent.

According to the exemplary embodiments of the present invention, a method of measuring a strain of a display device may be applied to various display devices. Thus, a reliability of the display device may be improved.

The foregoing is illustrative of the invention and is not to be construed as limiting thereof. Although a few exemplary embodiments of the invention have been described, those skilled in the art will readily appreciate that many modifications are possible in the exemplary embodiments without materially departing from the novel teachings and advantages of the invention. Accordingly, all such modifications are intended to be included within the scope of the invention as defined in the claims. In the claims, means-plus-function clauses are intended to cover the structures described herein as performing the recited function and not only structural equivalents but also equivalent structures. Therefore, it is to be understood that the foregoing is illustrative of the invention and is not to be construed as limited to the specific exemplary embodiments disclosed, and that modifications to the disclosed exemplary embodiments, as well as other exemplary embodiments, are intended to be included within the scope of the appended claims. The invention is defined by the following claims, with equivalents of the claims to be included therein.

What is claimed is:

1. A method of measuring a strain experienced by a display device, the method comprising:
   coating a measurement pigment composition comprised of pigment particles on any portion of a surrounding non-display area of a display panel, a strain measuring part being defined by the measurement pigment composition coating, the surrounding non-display area of the display panel consisting of display panel surfaces not covered by device components interfacing with the display panel, the strain measuring part comprising at least one selected from the group consisting of an ultraviolet curable resin, a thermoplastic resin and a thermosetting resin;
   obtaining a first three-dimensional image of the strain measuring part;
   causing a shape of the strain measuring part to change by bending at least one portion of the display device including the display panel;
   obtaining a second three-dimensional image of the strain measuring part; and
   generating a strain of the display device by making a comparison between a plurality of the three-dimensional images of the strain measuring part.

2. The method of claim 1, further comprising:
   combining a polarization film with the display panel; and
   combining a driving part with the display panel at a side of the polarization film.

3. The method of claim 2, wherein the surrounding area of the display panel comprises a first coating area, a second coating area, and a third coating area, and wherein the first coating, area surrounds the driving pan, the second coating area surrounds the polarization film, and the third coating area is on a lower surface of the display panel, which is opposite to an upper surface of the display panel where the polarization film and the driving part are disposed.

4. The method of claim 1, wherein the measurement pigment composition is coated by a dispensing, a screen printing, a spin coating, a slit coating, a bar coating, or a nozzle spraying to form the strain measuring part.

5. The method of claim 1, wherein the pigment particles comprise a black pigment particle and a white pigment particle.

6. The method of claim 1, the measurement of the strain of the display device comprising:
   taking the first three-dimensional image of the display device before the display device is bent;
   taking the second three-dimensional image of the display device after bending the display device;
   comparing the first three-dimensional image with the second three-dimensional image; and
   using a processing computer and software to determine the strain of the display device based on the comparison between the first three-dimensional image and the second three-dimensional image.

7. The method of claim 6, wherein the bending of the display device is controlled by an operator.

8. The method of claim 1, the method being comprised of obtaining the comparison by measuring distances between the pigment particles for the first and second three-dimensional images.

9. The method of claim 1, further comprising the measuring of the strain using a three-dimensional (3D) image camera.

10. A display device, comprising:
    a display panel; and
    a strain measuring part comprising pigment particles disposed on an area surrounding the display panel to provide a representation of strain experienced by the area surrounding the display panel, strain experienced by the display device being amenable to measurement by comparing three-dimensional images of the strain measuring part, the surrounding area of the display panel comprised of display panel surfaces not covered by device components interfacing with the display panel, the three-dimensional images being obtained before and after bending of the display panel, the strain measuring part comprising at least one selected from the group consisting of an ultraviolet curable resin, a thermoplastic resin and a thermosetting resin.

11. The display device of claim 10, wherein the pigment particles comprises at least one selected from the group consisting of lithopone, white lead, and carbon black.

12. The display device of claim 10, the pigment particles comprising at least one selected from the group consisting of $K_2O$, $Fe_2O_3$, $Sb_2O_3$, $ZnO$, $P_2O_5$, $V_2O_5$, $TiO_2$, $Al_2O_3$, $WO_3$, $SnO$, $PbO$, $MgO$, $CaO$, $BaO$, $Li_2O$, $Na_2O$, $B_2O_3$, $TeO_2$, $SiO_2$, $Ru_2O$, $Rh_2O$, $CuO$, $Cr_2O_3$, $Na_2S$, and $Bi_2O_3$.

13. The display device of claim 10, wherein a size of each pigment particle is about 0.1 µm to about 0.5 µm.

14. The display device of claim 10, a. thickness of the display panel is about 100 µm to about 500 µm.

15. The display device of claim 10, further comprising a polarization film disposed on the display and a driving part connected to the display panel.

16. The display device of claim 10, wherein the strain measuring part is disposed on an upper surface of the display panel to have a shape surrounding the polarization film in a plan view.

17. The display device of claim 16, wherein the strain measuring part is further disposed on a lower surface of the display panel.

18. The display device of claim 10, wherein the strain measuring part is coupled with a three-dimensional (3D) image camera to obtain the representation of the strain.

19. A method of measuring a strain experienced by a display, the method comprising:
    coating a measurement pigment composition comprised of pigment particles on an portion of a surrounding non-display area of a display panel, a strain measuring part being defined by the coating of measurement pigment composition, the surrounding non-display area of the display panel comprised of display panel surfaces not covered by device components interfacing with the display panel;
obtaining a first three-dimensional image of the strain measuring part;
bending at least one portion of the display device including the display panel, the bending causing a shape of the strain measuring part to change by the bending;
obtaining a second three-dimensional image of the strain measuring part;
comparing a plurality of the three-dimensional images of the strain measuring part to generate a strain measurement; and
using the measured strain Of the display device iteratively to design a display device including a display panel having a desired strain ratio in response to a selected external pressure, where delamination of any films disposed on or under the display panel is prevented.

* * * * *